US011583367B2

(12) United States Patent
Bühler et al.

(10) Patent No.: US 11,583,367 B2
(45) Date of Patent: Feb. 21, 2023

(54) METHOD FOR PRODUCING A GUIDED BIT GUARD, AND GUIDED BITE GUARD

(71) Applicant: SIRONA DENTAL SYSTEMS GMBH, Bensheim (DE)

(72) Inventors: Elias Bühler, Zurich (CH); Thomas Oskam, Zurich (CH); Evangelos Makris, Zurich (CH)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 16/648,099

(22) PCT Filed: Oct. 2, 2018

(86) PCT No.: PCT/EP2018/076780
§ 371 (c)(1),
(2) Date: Mar. 17, 2020

(87) PCT Pub. No.: WO2019/068703
PCT Pub. Date: Apr. 11, 2019

(65) Prior Publication Data
US 2020/0275995 A1    Sep. 3, 2020

(30) Foreign Application Priority Data
Oct. 2, 2017 (DE) .......................... 102017217558.3

(51) Int. Cl.
*A61C 7/08*    (2006.01)
*A61C 7/00*    (2006.01)
(Continued)

(52) U.S. Cl.
CPC ............... *A61C 7/08* (2013.01); *A61C 7/002* (2013.01); *A61C 11/00* (2013.01); *A61C 13/34* (2013.01); *A61C 19/05* (2013.01)

(58) Field of Classification Search
CPC .. A61C 7/08; A61C 7/002; A61C 7/36; A61C 5/007; A61C 13/34; A61C 13/0004;
(Continued)

(56) References Cited

U.S. PATENT DOCUMENTS 6,152,731 A * 11/2000 Jordan ............... A61C 13/0003
433/69
7,474,932 B2 * 1/2009 Geng ..................... G16Z 99/00
700/98
(Continued)

FOREIGN PATENT DOCUMENTS

DE    202004020196 U1    5/2005
DE    202010006250 U1    9/2010
(Continued)

OTHER PUBLICATIONS

Morgado, Pilar & Diaz Lantada, Andres & Martinez-Alvarez, Alexander & Barrientos, Antonio & Yustos, Héctor & Cepeda, Pedro & González, Roberto & Muñoz-Garcia, Julio & Otero, Javier. (2008). Instrumented Splint for the Diagnosis of Bruxism . . . BIODEVICES 2008 (Year: 2008).*
(Continued)

*Primary Examiner* — Ralph A Lewis
(74) *Attorney, Agent, or Firm* — Dentsply Sirona Inc.

(57) ABSTRACT

The invention relates to a method for producing a guided bite splint for a supporting jaw comprising at least one guide for an opposing jaw. A 3D model of an upper jaw and/or a 3D model of a lower jaw are available, wherein the 3D models of the upper jaw and the lower jaw are arranged relative to one another in an occlusal position and integrated into a virtual articulator model which simulates an articulation movement of the lower jaw relative to the upper jaw, wherein a 3D model of the bite splint is constructed using the 3D model of the upper jaw and/or the 3D model of the lower jaw, wherein the at least one guide for the opposing
(Continued)

jaw is constructed automatically on the 3D model of the bite splint with the aid of a computer.

9 Claims, 1 Drawing Sheet

(51) Int. Cl.
*A61C 11/00* (2006.01)
*A61C 13/34* (2006.01)
*A61C 19/05* (2006.01)

(58) Field of Classification Search
CPC ..... A61C 13/0013; A61C 11/02; A61C 19/05; A61C 11/00–088; A61C 19/045; A61F 5/566; A61F 2005/563; A61F 2/3094; A61F 2/30942; A61F 2/309; A61F 2/43; A61F 2/30952
USPC ....... 433/6, 19, 24, 214; 128/8; 700/98, 118, 700/97
See application file for complete search history.

(56) References Cited

U.S. PATENT DOCUMENTS

| | | | | |
|---|---|---|---|---|
| 7,835,811 | B2* | 11/2010 | Schmitt | G16H 50/50 700/98 |
| 9,730,768 | B2* | 8/2017 | Lucas | A61C 5/007 |
| 9,848,965 | B2* | 12/2017 | Kim | A61C 9/0006 |
| 9,877,812 | B2* | 1/2018 | Wouters | B29C 64/386 |
| 9,931,177 | B2* | 4/2018 | Wouters | A63B 71/085 |
| 10,537,406 | B2* | 1/2020 | Wu | A61C 7/36 |
| 2004/0172150 | A1* | 9/2004 | Perot | A61C 9/004 700/98 |
| 2005/0022824 | A1* | 2/2005 | Ball | A61F 5/566 128/861 |
| 2009/0305185 | A1* | 12/2009 | Lauren | A61C 9/0053 433/29 |
| 2010/0076581 | A1* | 3/2010 | Violante | A61C 13/0004 700/98 |
| 2012/0065756 | A1* | 3/2012 | Rubbert | A61C 8/0048 700/98 |
| 2014/0370465 | A1* | 12/2014 | Lucas | A61C 7/36 433/214 |
| 2015/0238280 | A1* | 8/2015 | Wu | A61C 7/36 433/6 |
| 2015/0238289 | A1* | 8/2015 | Wouters | B29C 64/386 700/98 |
| 2015/0238290 | A1* | 8/2015 | Wouters | B29C 64/386 700/98 |
| 2016/0166362 | A1* | 6/2016 | Nonboe | A61C 9/004 703/1 |
| 2020/0197137 | A1* | 6/2020 | Xia | A61B 34/20 |
| 2020/0268495 | A1* | 8/2020 | Ryakhovsky | A61C 11/00 |

FOREIGN PATENT DOCUMENTS

| | | |
|---|---|---|
| DE | 102013112032 A1 | 4/2015 |
| EP | 1516604 A1 | 3/2005 |
| WO | 2011131243 A1 | 10/2011 |
| WO | 2012140021 A2 | 10/2012 |
| WO | 2017125799 A1 | 7/2017 |

OTHER PUBLICATIONS

Hungate, Ryan.University of Southern California. ProQuest Dissertations Publishing, 2015. 10799522. (Year: 2015).*
Zinser MJ, Mischkowski RA, Sailer HF, Zöller JE. Computer-assisted orthognathic surgery: feasibility study using multiple CAD/CAM surgical splints. Oral Surg Oral Med Oral Pathol Oral Radiol. May 2012;113(5):673-87. doi: 10.1016/j.oooo.2011.11.009. Epub Apr. 12, 2012. PMID: 22668627. (Year: 2011).*
J. Chapuis et al., "A New System for Computer-Aided Preoperative Planning and Intraoperative Navigation During Corrective Jaw Surgery," in IEEE Transactions on Information Technology in Biomedicine, vol. 11, No. 3, pp. 274-287, May 2007, doi: 10.1109/TITB.2006.884372. (Year: 2007).*
Berntsen, Christian et al. "Clinical comparison of conventional and additive manufactured stabilization splints." Acta biomaterialia odontologica Scandinavica vol. 4,1 81-89. Aug. 13, 2018, doi:10.1080/23337931.2018.1497491 (Year: 2018).*
Palazzo, Giuseppe et al. "Comparison between Additive and Subtractive CAD-CAM Technique to Produce Orthognathic Surgical Splints: A Personalized Approach." Journal of personalized medicine vol. 10,4 273. Dec. 11, 2020, doi:10.3390/jpm10040273 (Year: 2020).*
International Search Report; PCT/EP2018/076780; Dec. 19, 2018 (completed); dated Jan. 7, 2019.
Written Opinion of the International Searching Authority; PCT/EP2018/076780; Dec. 19, 2018 (completed); dated Jan. 7, 2019.
International Preliminary Report on Patentability; PCT/EP2018/076780; Dec. 19, 2018 (completed); dated Jan. 7, 2019.
European Office Action dated Jun. 15, 2021.

* cited by examiner

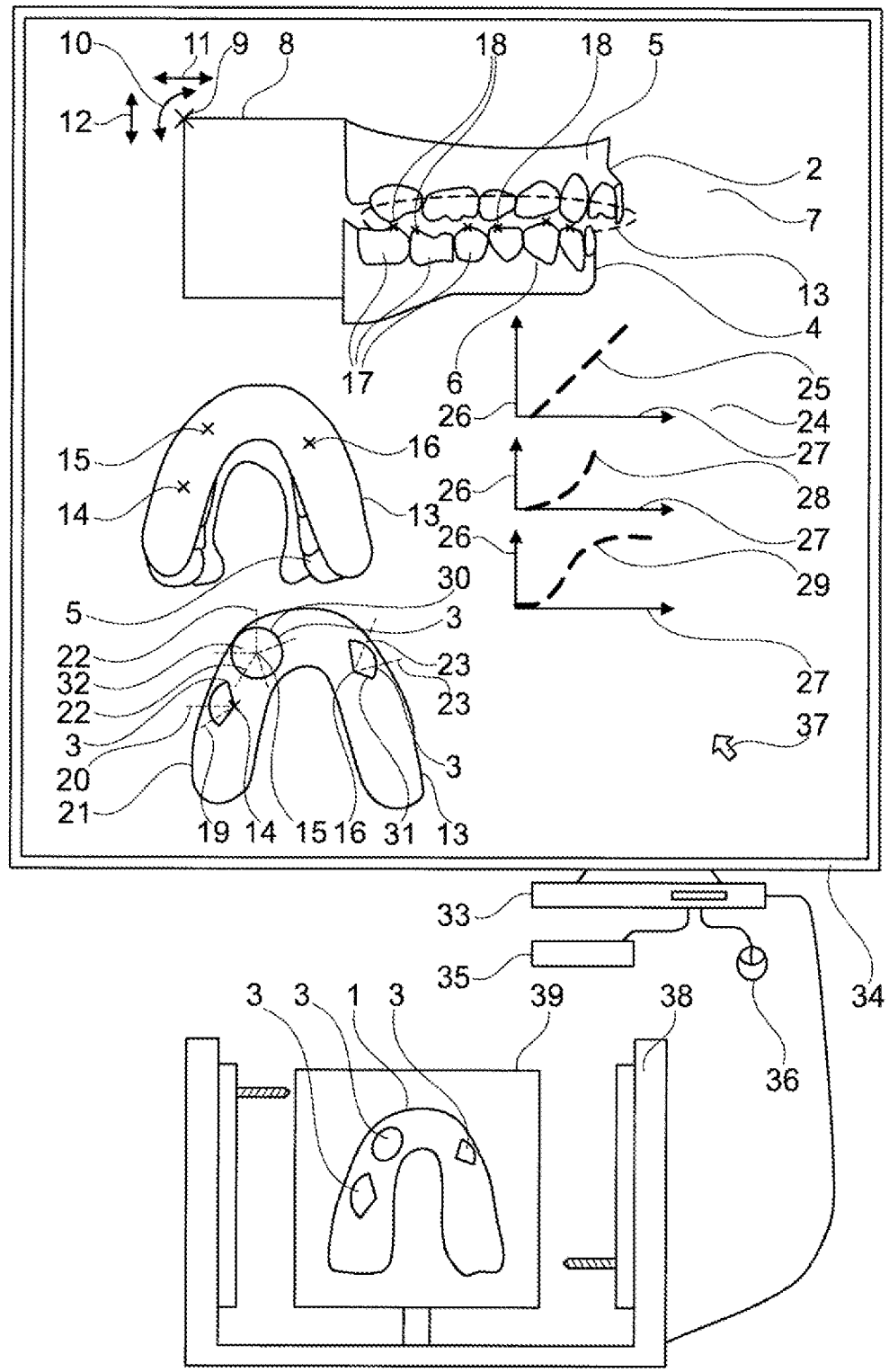

METHOD FOR PRODUCING A GUIDED BIT GUARD, AND GUIDED BITE GUARD

TECHNICAL FIELD

The invention relates to a method for producing a guided bite splint for a supporting jaw comprising at least one guide for an opposing jaw.

BACKGROUND OF THE INVENTION

From the state of the art, production methods for a guided bite splint are known, in which a guided bite splint is clamped into an articulator and gradually adjusted. In particular the guide tracks are produced mechanically step-by-step using an articulation movement in the articulator, in which the material is gradually removed manually.

DE 20 2010 006 250 U1 discloses a device for producing a guide rail for correcting the condylar position of a temporomandibular joint, whereby the device comprises a positionally variable platform on which a lower jaw model is arranged and the position of which relative to the upper jaw model is changed using a control device.

DE 10 2013 112 032 A1 discloses a method for constructing a bite splint, wherein 3D data of the two jaws is acquired, and the position of the jaws and the temporomandibular joints of the patient relative to one another is acquired, wherein an occlusion is simulated, wherein dental interfering contacts of a craniomandibular system are identified and a bite splint is constructed using the acquired 3D data and from the simulation of the obtained data, so that the identified interfering contacts are eliminated. In order to avoid pain, a series of multiple bite splints is constructed to interactively approximate the physiological position of the temporomandibular joints, whereby the bite splints of the series differ only slightly in their shape and the temporomandibular joints are thus brought into their physiological position in small discrete steps over a longer period of time.

US 2015/0238280 A1 discloses a device and method for positioning the jaws for jaw correction, wherein a treatment plan is provided, wherein a virtual model of a dental device comprises a first shell and a second shell configured to reposition the two jaws of the patient. A first element can be attached to the upper shell and a second element can be attached to the lower shell, wherein the two elements come into contact with one another to bring about a desired displacement of the two jaws.

EP 1516604 A1 discloses an intraoral therapy device, preferably a snore therapy device, having an upper jaw splint and a lower jaw splint, wherein the two splints are connected to one another in an articulated manner with a fixed rod.

One disadvantage of the known methods is that the guides of a guided bite splint are added later by manual reworking.

The object of the present invention is therefore to provide a method for producing a guided bite splint which allows a precise and time-saving production of a guided bite splint, whereby manual production errors, in particular of the guides of the bite splint, are to be avoided.

SUMMARY OF THE INVENTION

The invention relates to a method for producing a guided bite splint for a supporting jaw comprising at least one guide for an opposing jaw. A 3D model of an upper jaw and/or a 3D model of a lower jaw are already available, whereby the 3D models of the upper jaw and the lower jaw are arranged in an occlusal position relative to one another. Subsequently, using the 3D model of the upper jaw and/or the 3D model of the lower jaw, a 3D model of the bite splint is constructed, whereby the at least one guide for the opposing jaw is automatically constructed on the 3D model of the bite splint with the aid of a computer.

The guided bite splint is constructed on the upper jaw as a supporting jaw and thus as the opposing jaw for the lower jaw, or on the lower jaw as a supporting jaw and thus as the opposing jaw for the upper jaw.

A guided bite splint is used in the dental and orthodontic treatment of teeth grinding, bruxism and craniomandibular dysfunction, and also as a mouthguard.

A guided bite splint can be a Michigan splint, for example, which is used to prevent muscle and joint pain and unstable terminal occlusion. The Michigan splint acts primarily as a relaxation splint. The guidance of the lower jaw on the bite splint is most often carried out in the area of the cuspids.

The guided bite splint can also be a DROS® Bite splint, which is used in particular for mandibular stabilization.

The guided bite splint therefore serves as a relaxation splint to prevent occlusal malfunctions and to relax the masticatory muscles (reduction of muscle tone). The guided bite splint is also intended to protect against destruction of the hard tooth substance caused by teeth grinding.

A guided bite splint can be used to treat different malocclusions, such as a malocclusion with a receding lower jaw or a malocclusion with a protruding lower jaw. The jaw abnormalities can either be congenital or acquired. The extent of the malocclusion only becomes apparent when the jaw is closed and is evidenced by an open bite, for example, or by the fact that the teeth of the upper jaw bite behind the teeth of the lower jaw instead of the other way around. The position of the jaws to one another and to the facial bones has a significant impact on the facial profile. Depending on whether the overdevelopment or underdevelopment is located in the upper jaw and/or in the lower jaw, different facial profiles result alongside the malocclusion.

The guide of the bite splint is usually disposed in the area of the front teeth and/or in the area of the cuspids and can have a specific angle of inclination relative to an insertion axis of the bite splint between 20 and 40 degrees, usually in the lateral direction and/or protrusal direction of a jaw movement.

The 3D models of the upper jaw and/or the lower jaw are already available for carrying out said method and were, for example, measured using an intraoral 3D camera.

The 3D models of the two jaws are arranged in the occlusal position to one another and integrated into a virtual articulator model. A lateral 3D image of the two jaws of the patient in terminal occlusion, for example, can be used to arrange the two 3D models relative to one another.

The at least one guide for the opposing jaw is constructed automatically with the aid of a computer, whereby, in terminal occlusion, the guide of the bite splint exerts a force in a desired direction on the opposing jaw to correct the malocclusion.

In the case of a protruding lower jaw, the lower jaw should be moved in a distal direction toward the end of the dental arch to correct the malocclusion. In the case of a receding lower jaw, the lower jaw should be moved in a mesial direction toward the center of the dental arch.

One advantage of the present method is that the guided bite splint is virtually constructed with the aid of a computer, and can be produced fully automatically according to the constructed 3D model of the guided bite splint using a CAD/CAM method or using a 3D printer.

A further advantage of the present method is that the at least one guide of the guided bite splint can be accurately positioned and precisely adapted to the opposing jaw. In comparison to the known production methods, the time-consuming step-by-step removal of the material to produce the guides is eliminated.

The 3D models of the upper jaw and the lower jaw can advantageously be integrated into a virtual articulator model, which simulates an articulation movement of the lower jaw relative to the upper jaw.

The virtual articulator model simulates an articulator, which mimics the movement of the temporomandibular joint. The movement of the jaws relative to one another is simulated, whereby the temporomandibular joint can carry out both rotational movements (opening and closing movements about the axis of the joint) and sliding movements (forward movements). The temporomandibular joints consist of a cartilage-covered joint head, a likewise cartilage-covered joint cavity and the fibrocartilaginous intermediate joint disc. The temporomandibular joint further consists of soft tissue structures such as the ligamentous apparatus, vessels and nerves. When the mouth is opened, the joint head slides forward and down together with the disc, which is normally firmly attached to the joint head. The temporomandibular joints and the masticatory muscles are active in all movements of the lower jaw. The intent is to mimic these movements with the aid of the virtual articulator model. To create the virtual articulator model, the relative positions of the two jaws to one another can be measured for different opening angles, for example, and transferred accordingly to the virtual articulator model.

The guided bite splint is then constructed in the virtual articulator model with the aid of a computer using the two 3D models of the jaws and taking into account the simulated movements of the temporomandibular joints.

As an alternative to the virtual articulator model, the movements of the two jaws relative to one another can also be calculated or simulated using so-called heuristics, for example a translational movement of the two 3D models of the jaws toward one another.

The extension of the guided bite splint on the upper jaw or on the lower jaw as the supporting jaw can advantageously be set automatically or by a user with the aid of a computer.

The extension of the guided bite splint relative to the supporting jaw is thus set. The extension can be set by the user using a virtual tool, by drawing the boundary of the guided bite splint onto the 3D model of the supporting jaw. The extension of the bite splint can alternatively be set automatically with the aid of a computer by accessing a database of different 3D models of supporting jaws and selecting a suitable 3D model of a supporting jaw for which the extension of the bite splint has already been defined.

A minimum thickness of the guided bite splint can advantageously be set automatically or by a user with the aid of a computer.

The minimum thickness of the bite splint can thus be set. The user can, for example, enter the value for the minimum thickness manually. The minimum thickness can alternatively be set automatically with the aid of a computer by comparing the measured 3D model of the supporting jaw with the database of different supporting jaws for which minimum thicknesses have already been specified. The guided bite splint has to have the specified minimum thickness everywhere along an insertion axis of the bite splint. The insertion axis is defined by an insertion direction when the bite splint is placed on the supporting jaw. The thickness towards the edge of the bite splint can be less than the specified minimum thickness, however.

A defined distance of an occlusion opening in a desired occlusal position of the guided bite splint can advantageously be set automatically or by a user with the aid of a computer.

The defined distance of the occlusion opening is thus defined. The distance can be entered by a user, for example, or compared to a database of different supporting jaws and opposing jaws having known occlusion openings automatically with the aid of a computer. For example, the distance of the occlusion opening can be defined by the distance between the corresponding occlusion contacts of the supporting jaw and the opposing jaw.

The 3D model of the guided bite splint is calculated automatically with the aid of a computer, wherein the conditions must be satisfied that the guided bite splint covers a defined contact area on the supporting jaw and that at least one local cusp tip is defined as a support point for at least one tooth of the opposing jaw.

The 3D model of the guided bite splint is thus calculated automatically with the aid of a computer such that the conditions are satisfied. The defined contact area can be determined manually by a user, or automatically with the aid of a computer by comparing it to a database of different supporting jaws. The defined support point for the individual teeth ensures a stable mechanical placement of the bite splint on the supporting jaw.

At least one guide point of the guide to be constituted on the opposing jaw can advantageously be defined automatically with the aid of a computer or manually by a user.

The guide point is thus defined manually by the user using a virtual tool or automatically with the aid of a computer, by comparing it to a database of different supporting jaws and opposing jaws having set guide points.

Advantageously, at least one movement profile can be defined for each guide point.

The user thus defines a movement profile for each guide point, for example with the aid of a virtual tool. The movement profile is defined as a function of the jaw opening in dependence of a jaw movement distance. The movement profile thus defines a desired movement path of the opposing jaw as the jaw opening is reduced to a closed occlusal position, in which the opposing jaw bites down on the bite splint. To obtain the desired movement path, for example in the case of a protruding lower jaw, a force is exerted on the lower jaw in a distal direction and, in the case of a receding lower jaw, a force is exerted in a mesial direction. The movement profile passes through a fixed plane, which in turn passes through the guide point and, for example, extends along a direction of the insertion axis. It is also possible to define multiple movement profiles in different planes for one guide point.

The surface shape of the guide can advantageously be calculated automatically with the aid of a computer as a function of the at least one movement profile.

The surface shape of the guide is thus calculated automatically with the aid of a computer as a function of at least one set movement profile. The surface of the 3D model of the guided bite splint can be adjusted or guided accordingly in the areas of the guides, whereby an intermediate space between the set movement profiles can be interpolated in such a way that a smooth transition of the surface shape of the guide is produced. The surface shape of the guide is therefore calculated such that the constructed guide brings about the desired movement path of the opposing jaw relative to the bite splint and relative to the supporting jaw in accordance with the defined movement profiles.

Advantageously, at least two movement profiles can be defined in two different planes for each guide point, whereby the surface shape of the guide between the two planes of the two movement profiles is interpolated in such a way that a smooth transition is produced.

The interpolation between the movement profiles thus results in a smooth transition of the surface shape of the guide, whereby the desired movement path of the opposing jaw relative to the supporting jaw is achieved by the constructed guide.

A first plane of a first movement profile can be disposed in a lateral movement direction, for example, and a second plane of a second movement profile can, for example, be disposed in a protrusional (back and forth) movement direction.

During the construction of the bite splint, the surface of the virtual 3D model of the guided bite splint can advantageously be reduced to such an extent that no surface point of the 3D model of the opposing jaw is virtually penetrated as long as the opposing jaw is moved along the at least one guide in the virtual articulator model within a defined range of movement.

The 3D model of the guided bite splint is thus reduced to the extent that the guided bite splint only comes into contact with the opposing jaw at the defined guides and, in the defined occlusal position, at the defined contact areas, so that interfering areas of the bite splint are reduced or eliminated. Later manual processing of the bite splint to reduce the interfering areas is therefore not necessary.

The guided bite splint can advantageously be produced fully automatically according to the constructed 3D model of the bite splint using a subtractive manufacturing method, such as a CAM machine, or using an additive manufacturing method, such as a 3D printer.

The guided bite splint is thus produced fully automatically according to the constructed 3D model.

For production using a CAM machine, a blank is clamped into the CAM machine and processed by means of milling tools and/or grinding tools until the guided bite splint is produced according to the constructed 3D model. When using a 3D printer, the constructed bite splint is printed. The 3D printer can be based on an SLS method (selective laser sintering), for example, which allows the printing of three-dimensional objects without binding agents or additional assembly steps. The existing 3D model of the bite splint is broken down into numerous horizontal planes by means of special slicing software and passed on to the 3D printer as control commands. The 3D printer then prints the object layer by layer, whereby individual powder particles in a powder bed are fused together with a high temperature of the laser. The object is then lowered and a new powder layer is applied. The process is repeated until the entire guided bite splint is completely printed. The 3D printer can also be based on a stereolithography method, in which a laser is used to polymerize a mass composed of photosensitive resin and material particles. The material of the guided bite splint can, for example, be a plastic having a suitable hardness. The hardness and the elasticity of the plastic are selected such that a precise guidance of the opposing jaw along the constructed guides is made possible. The bite splint can also be made of a variety of plastics.

A further object of the invention is the guided bite splint produced using the above-mentioned method, whereby the at least one guide for the opposing jaw is constructed automatically with the aid of a computer.

The advantage of such a guided bite splint is that the guides are positioned exactly in order to ensure a defined movement path relative to the supporting jaw or to the bite splint.

The guide for the opposing jaw can advantageously be constructed using the at least one movement profile at at least one guide point.

The guide is thus constructed using the defined movement profile, so that the guide brings about the desired movement path of the opposing jaw.

The guided bite splint can advantageously be produced fully automatically according to the constructed 3D model of the bite splint using a subtractive manufacturing method, such as a CAM machine, or using an additive manufacturing method, such as a 3D printer.

The guided bite splint is thus produced fully automatically and consequently in a time-saving manner, whereby production errors of the guides that can occur when the bite splint is produced manually are avoided.

BRIEF DESCRIPTION OF THE DRAWINGS

The invention will be explained with reference to the drawings. The drawings show:

FIG. 1 a sketch to illustrate the method for producing a guided bite splint.

DETAILED DESCRIPTION OF THE INVENTION

FIG. 1 shows a sketch to illustrate the method for producing a guided bite splint 1 for a supporting jaw 2, in the present case for the upper jaw, comprising at least one guide 3. In the present case, the bite splint 1 comprises multiple guides 3 with the opposing jaw 4, in the present case for the lower jaw. A 3D model 5 of the upper jaw and a 3D model 6 of the lower jaw are already available and were measured on the patient with the aid of an intraoral 3D camera. The 3D model 5 of the upper jaw and the 3D model 6 of the lower jaw are arranged in an occlusal position 7 relative to one another and integrated into a virtual articulator model 8. The articulator model 8 simulates an articulation movement of the temporomandibular joint 9, which is shown as a cross for clarification, and thus of the lower jaw 6 relative to the upper jaw 5. The articulation movement of the temporomandibular joint 9 can be composed of a rotational movement 10, a forward movement 11 in horizontal direction, a movement 12 in vertical direction relative to the 3D model 5 of the upper jaw, and a not depicted lateral movement in a rotational axis direction of the temporomandibular joint 9. A 3D model 13 of the guided bite splint 13 is then constructed using the 3D model 5 of the upper jaw 2, the 3D model 6 of the lower jaw 4, and using the simulated movement path of the lower jaw 4 relative to the upper jaw 2 from the articulator model 8. Subsequently, a first guide point 14, a second guide point 15 and a third guide point 16 are set on the 3D model 13 of the bite splint 1 manually by a user or automatically with the aid of a computer. The guide points 14, 15, and 16 on the 3D model 13 of the bite splint are set relative to their positions on the opposing jaw 4. The extension of the 3D model 13 of the bite splint 1 relative to the 3D model 5 of the supporting jaw 2 is set manually by the user or automatically with the aid of a computer in such a way that at least one defined contact area of the supporting jaw 2 is covered and an opening of the jaw has a defined value. The 3D model 13 of the bite splint 1 is constructed in such a way that a local cusp tip is defined as a support point 18 for every tooth 17 of the opposing jaw 4. The support points 18 are depicted as crosses on the opposing teeth 17. For the first guide point 14, a first movement profile 19 is set in a first plane, a second movement profile 20 is set in a second plane and a third profile 21 is set in a third plane. Multiple movement profiles 22 are defined in different planes for the second guide point 15 as well. Likewise, two movement profiles 23 are defined in different planes for the third guide point 16. A first diagram 24 shows an example for a first function 25 of the first movement profile 19 as a function of an opening 26 of the opposing jaw 4, namely a distance between the jaws, and depending on a distance 27 of the respective sliding contact point of the opposing jaw in the guide relative to the respective guide point in the plane of the respective movement profile. The first function 25 for the first movement profile 19 has a linear progression. A second function 28 of the second movement profile 20 has an exponential progression. A third function 29 of the third movement profile 21 has an S-shaped progression. The surface shape of the first guide 3 is calculated automatically with the aid of a computer depending on the movement profiles 19, 20 and 21 of the first guide point 14. The second guide 30 is calculated depending on the five movement profiles 22 of the second guide point 15. The third guide 31 is calculated depending on the movement profiles 23 of the third guide point 16. The surface shape of the guide 3, 30, 31 is interpolated in an intermediate area 32 between adjacent movement profiles, so that a smooth transition of the surface shape of the guide is produced. The construction of the guided bite splint is carried out virtually using a computer 33, whereby a display device 34, such as a monitor, and operating elements, such as a keyboard 35 and a mouse 36, are connected to the computer 33. The construction of the 3D model 13 of the bite splint 1 can be carried out automatically with the aid of a computer and/or manually by a user using a virtual tool 37, such as a cursor. Once the construction of the 3D model 13 of the bite splint 1 is complete, the construction data is forwarded to a CAM machine 38. In the CAM machine 38, the guided bite splint 1 to be produced with the guides 3 is then ground out of a blank 39, which can be made of a special plastic. The guided bite splint 1 can alternatively also be produced using a 3D printer.

REFERENCE SIGNS

1 Bite splint
2 Supporting jaw
3 Guides
4 Opposing jaw
5 3D model upper jaw
6 3D model of the lower jaw
7 Occlusal position
8 Articulator model
9 Temporomandibular joint
10 Rotational movement
11 Forward movement
12 Movement in vertical direction
13 3D model of the bite splint
14 First guide point
15 Second guide point
16 Third guide point
17 Teeth
18 Support points
19 First movement profile
20 Second movement profile
21 Third movement profile
22 Movement profiles
23 Movement profiles
24 Diagram
25 Function of the first movement profile
26 Opening of the opposing jaw
27 Distance of the contact point
28 Function of the second movement profile
29 Function of the third movement profile
30 Second guide
31 Third guide
32 Intermediate area
33 Computer
34 Display device
35 Keyboard
36 Mouse
37 Cursor
38 CAM machine
39 Blank

What is claimed is:

1. A method comprising:
    providing a 3D model of an upper jaw and a 3D model of a lower jaw; arranging the 3D models of the upper jaw and the lower jaw relative to one another in an occlusal position;
    constructing a 3D model of a guided bite splint for a supporting jaw using the 3D model of the upper jaw, the 3D model of the lower jaw and a desired movement path of an opposing jaw relative to the supporting jaw;
    setting, on said 3D model of the guided bite splint, and responsive to the constructing, at least one guide point, said at least one guide point being set relative to a position of the at least one guide point on the opposing jaw;
    defining at least one movement profile for the at least one guide point, said at least one movement profile being defined as a function of a jaw opening and said at least one movement profile being representative of the desired movement path of the opposing jaw as the jaw opening is reduced to a closed occlusal position; and
    automatically computing, on the 3D model of the guided bite splint, a surface shape of the at least one guide for the opposing jaw based on at least two movement profiles of the defined at least one movement profile of the at least one guide point by defining said at least two movement profiles in two different planes for a guide point of the at least one guide point and interpolating the surface shape of the at least one guide between the two different planes in such a way that a smooth transition is produced;
    wherein said at least one guide for the opposing jaw brings about said desired movement path of the opposing jaw;
    wherein conditions must be satisfied such that the guided bite splint covers a defined contact area on the supporting jaw and that at least one local cusp tip is defined as a support point for at least one tooth of the opposing jaw,
    wherein when the upper jaw is the supporting jaw, the lower jaw is the opposing jaw and vice versa; and
    wherein the method further comprises manufacturing the guided bite splint based on the 3D model of the guided bite splint.

2. The method according to claim 1, further comprising the step of integrating the 3D models of the upper jaw and the lower jaw into a virtual articulator model which simulates an articulation movement of the lower jaw relative to the upper jaw.

3. The method according to claim 1, further comprising setting, automatically or by a user with the aid of a computer, an extension of the guided bite splint on the upper jaw or on the lower jaw as the supporting jaw.

4. The method according to claim 1, further comprising setting, automatically or by a user with the aid of a computer, a minimum thickness of the guided bite splint.

5. The method according to claim 1, further comprising setting, automatically or by a user with the aid of a computer, a defined distance of an occlusion opening in a desired occlusal position of the guided bite splint.

6. The method according to claim 1, wherein, during the construction of the 3D model of the guided bite splint, the surface of the 3D model of the guided bite splint is reduced such that no surface point of the 3D model of the opposing jaw is virtually penetrated by the surface of the 3D model of the guided bite splint as the said 3D model of the opposing jaw is moved along the at least one guide in the virtual articulator model within a defined range of movement.

7. The method according to claim 6, wherein during said automatically computing, the surface of the 3D model of the guided bite splint only comes into contact with the 3D model of opposing jaw at the at least one guide and, in the occlusal position, at the defined contact area, such that interfering areas of the bite splint are reduced or eliminated and such that a subsequent manual processing of the bite splint to reduce the interfering areas is not necessary.

8. The method according to claim 1, wherein the guided bite splint is produced fully automatically using the constructed 3D model of the guided bite splint based on a subtractive manufacturing method or an additive manufacturing method.

9. The method according to claim 1, wherein the at least one local cusp tip is defined as the support point for every tooth of the opposing jaw.

* * * * *